United States Patent [19]

Arnold, III

[11] Patent Number: 4,995,556

[45] Date of Patent: Feb. 26, 1991

[54] UNITIZED SODIUM BICARBONATE DEODORIZER

[76] Inventor: Benjamin L. Arnold, III, 18695 Cambridge Rd., Lathrup Village, Mich. 48076

[21] Appl. No.: 148,004

[22] Filed: Jan. 25, 1988

[51] Int. Cl.$^5$ .............................. A61L 9/04; A61L 9/12
[52] U.S. Cl. ...................................... 239/57; 422/120; 422/122; 422/123
[58] Field of Search .................. 422/120, 122, 123, 5; 239/55-60, 51.5; 502/527, 400

[56] References Cited

U.S. PATENT DOCUMENTS

| | | | |
|---|---|---|---|
| 369,878 | 9/1887 | Palmer | 239/55 X |
| 477,217 | 6/1892 | McCoy | 239/55 |
| 1,780,408 | 11/1930 | Smith | 239/55 |
| 1,972,368 | 9/1934 | Alex | 239/55 |
| 2,025,657 | 12/1935 | Ganz | 239/55 |
| 2,215,988 | 9/1940 | Vivaudou et al. | 239/55 |
| 2,408,164 | 9/1946 | Foster | 502/527 X |
| 2,529,578 | 11/1950 | Thompson | 239/55 |
| 2,564,860 | 8/1951 | Ryberg | 239/55 X |
| 2,568,919 | 9/1951 | Kaye | 239/55 X |
| 2,720,419 | 10/1955 | Eby | 239/55 |
| 2,738,225 | 3/1956 | Meek | 239/55 |
| 2,766,067 | 10/1956 | Shinberg | 239/55 |
| 2,859,257 | 11/1958 | Hess et al. | 502/527 X |
| 3,129,888 | 4/1964 | O'Hagan | 239/55 |
| 3,343,664 | 9/1967 | Poitras | 239/56 X |
| 3,454,502 | 7/1969 | Hiltgen et al. | 502/527 X |
| 3,706,140 | 12/1972 | Brillaud et al. | 239/55 X |
| 3,924,807 | 12/1975 | Morgan | 239/55 |
| 3,958,949 | 5/1976 | Plantif et al. | 422/166 |
| 4,105,813 | 8/1978 | Mizuno | 239/57 X |
| 4,114,284 | 9/1978 | Weber et al. | 239/55 X |
| 4,194,690 | 3/1980 | Stever et al. | 239/57 |
| 4,203,388 | 5/1980 | Cortigene et al. | 119/1 |
| 4,220,281 | 9/1980 | Martens, III et al. | 239/57 |
| 4,233,161 | 11/1980 | Sato et al. | 239/60 X |
| 4,283,011 | 8/1981 | Spector | 239/57 X |
| 4,345,716 | 8/1982 | Armstrong et al. | 239/57 X |
| 4,704,989 | 11/1987 | Rosenfeld | 119/1 |

FOREIGN PATENT DOCUMENTS 3332525   3/1984   Fed. Rep. of Germany ........ 239/56

Primary Examiner—Barry S. Richman
Assistant Examiner—Amalia L. Santiago
Attorney, Agent, or Firm—Gifford, Groh, Sheridan, Sprinkle and Dolgorukov

[57] ABSTRACT

A unitized deodorizer for placement in restricted locations where odor control is desirable. The unitized deodorizer includes a portion of conventional sodium bicarbonate ($NaHCO_3$) or baking soda which is provided with or without a container. In its non-contained form, a unitized deodorizer is compressed or chemically bonded into a substantially solidified unit of selected shapes including round and block. In its contained form, pulverized sodium bicarbonate is provided within a number of containers composed of a variety of materials including plastic, flexibly woven natural or synthetic cloth, or cardboard.

3 Claims, 1 Drawing Sheet

UNITIZED SODIUM BICARBONATE DEODORIZER

BACKGROUND OF THE INVENTION

I. Field of the Invention

The present invention relates to unitized deodorizers. More particularly, the present invention relates to a unitized sodium bicarbonate deodorizer provided in either a contained or a non-contained form.

II. Description of the Relevant Art

In deodorizers for rooms, closets, refrigerators, and the like, such deodorizers are available in the form of sprays or powders. In these forms, use of the deodorizer inevitably leaves an undesirable residue which may be difficult to remove. Deodorizers are also provided in other forms and comprise a substance which sublimes to essentially mask odors. However, such deodorizers are relatively costly and are inconvenient to use.

Among deodorizers is also known the use of conventional baking soda or sodium bicarbonate ($NaHCO_3$). Conventionally, open containers of this substance are placed in refrigerators or the like to remove stale air. By exposing surface area of the compound to the atmosphere, odors are substantially adsorbed by the compound, thus filtering the atmosphere in the environment near the open box.

However, such use of sodium bicarbonate is impractical in that such boxes are inconveniently large and cumbersome and are therefore not suitable for use as deodorizing devices. If the sodium bicarbonate is removed from the box for local application, the problems discussed above with respect to powdered deodorizers and residue arise.

Accordingly, prior inventions have failed to eliminate the problems commonly associated with deodorizers.

SUMMARY OF THE PRESENT INVENTION

The present invention provides a unitized deodorizer for convenient manufacture, shipping and use. The unitized deodorizer according to the present invention overcomes all of the above-mentioned disadvantages of the previously known deodorizing devices thus providing the advantage of "setting a better mousetrap" for odors.

In brief, the unitized deodorizer of the present invention comprises a preselected amount of a deodorizing compound, such as between approximately 0.031 and 0.063 ounces, and having a preselected shape, such as round or block. The deodorizing compound is preferably sodium bicarbonate, $NaHCO_3$, preferably in pure form. The odor eliminating characteristics of sodium bicarbonate or baking soda are well known and the mechanism for odor elimination relies largely on the adsorption of odors from the atmosphere by the compound.

The present invention includes essentially two embodiments of the unitized deodorizer. The first embodiment is a solid deodorizer provided without a container and the second embodiment is in the form of a deodorizer having a container with pulverized deodorizing compound provided therein. In either embodiment, the large amount of surface area of the deodorizing compound exposed to the atmosphere provides a significant advantage over known uses of sodium bicarbonate, such as when a box of baking soda is left open in a refrigerator.

Either embodiment may be conveniently used in restricted areas, such as in shoes, closets, refrigerators, drawers, lockers, or just about any place in which undesirable odors are likely to arise.

BRIEF DESCRIPTION OF THE DRAWINGS

The various features, advantages and other uses of the present invention will become more apparent by referring to the following detailed description and drawings in which.

DETAILED DESCRIPTION OF THE PREFERRED EMBODIMENTS OF THE PRESENT INVENTION

Figure 1:
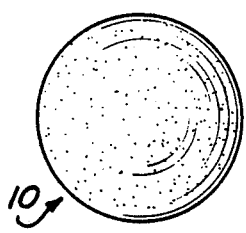
FIG. 1 is a perspective view of the unitized deodorizer of the present invention in a non-contained form having a round shape.

The drawings disclose preferred embodiments of the present invention. With reference first to FIG. 1, a preferred embodiment of the unitized deodorizer according to the present invention is thereshown having no container and having a round configuration and is generally indicated by 10. The containerless round deodorizer 10 is composed of compressed sodium bicarbonate. Alternatively, the sodium bicarbonate may be bonded by a selected binder which does not lessen odor adsorbing characteristics. As a preferred option, the sodium bicarbonate may be scented.

The deodorizer, in its solid form as shown in FIG. 1, may be formed in a number of different shapes. For example, and with reference to FIG. 2, the solid deodorizer may have a block shape, as illustrated by the containerless block deodorizer, generally indicated by 12.

Figure 2:
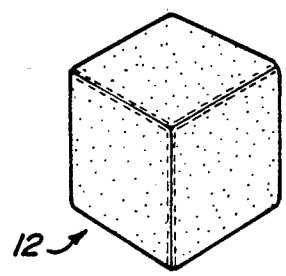
FIG. 2 is a perspective view of the unitized deodorizer in a non-contained form having a block shape.

In addition to being convenient to manufacture, ship and use, the solid form of the unitized deodorizer as shown in FIGS. 1 and 2 is also easily disposed of, and may be placed in a drain for freshening thereof. Because of the water solubility of sodium bicarbonate, no clogging of the drain results.

The unitized deodorizer may also be provided in contained forms, having substantially pulverized sodium bicarbonate contained therein. FIGS. 3–9 disclose unitized deodorizers according to the present invention provided in various containers composed of various materials, including plastic, flexibly woven natural or synthetic cloth, or cardboard.

Figure 3:
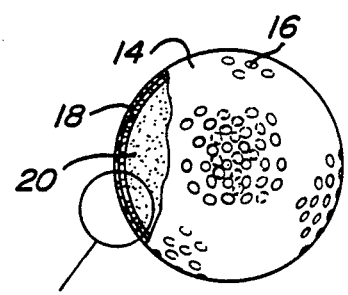
FIG. 3 is a perspective view of a unitized deodorizer of the present invention in a contained form showing a surface portion broken away.

Referring to FIG. 3, there is shown a preferred container for the unitized deodorizer having an outer shell 14 provided with a plurality of outer apertures 16. There is also provided coaxially with respect to the outer shell 14 an inner shell 18 which is more clearly seen in FIG. 3A. Within the inner shell 18 is provided a preselected amount of pulverized sodium bicarbonate compound 20.

Figure 3A:
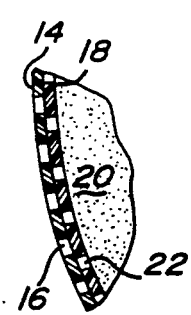
FIG. 3A is an enlarged segment of FIG. 3.

Referring to FIG. 3A for greater detail, the relationship of the outer shell 14 to the inner shell 18 is clearly shown. The inner shell 18, like the outer shell 14, is provided with a plurality of inner apertures 22. The outer apertures 16 and the inner apertures 22 are not aligned, thereby preventing the compound 20 from leaking. However, the construction permits air to bypass the outer shell 14 and the inner shell 18 by entering the outer apertures 16, following the joint between the outer shell 14 and the inner shell 18, which are fitted loosely together, and entering through the inner apertures 22 to the compound 20 contained therein.

Figure 4:
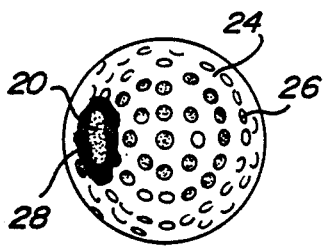
FIG. 4 is a perspective view showing an alternate embodiment of FIG. 3.

Referring to FIG. 4, there is shown an alternate container for the unitized deodorizer having a container shell 24 provided with a plurality of container shell apertures 26. The compound 20 is prevented from escaping through the apertures 26 by a screen mesh 28 which lines the inner side of container shell 24. While preventing the compound 20 from escaping the container shell 24, the screen mesh 28 permits air to pass to and through the compound 20.

Figure 5:
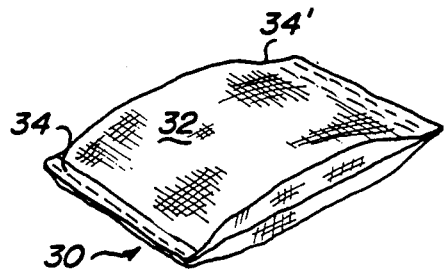
FIG. 5 is a perspective view of a unitized deodorizer having a woven container.

Referring to FIG. 5, there is shown a soft-shell version of the container for the unitized deodorizer according to the present invention. The soft container, generally indicated by 30, includes an outer flexibly woven closure 32 having stitchings 34, 34' at both ends. The closure 32 may be composed of a natural blend of material or of a polymerized material. In either form, the mesh of the closure 32 is fine enough so that air can enter, but compound (not visible) will not escape.

Figure 6:
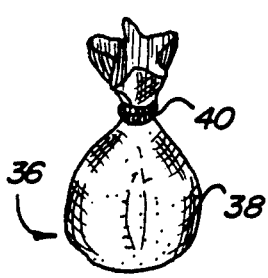
FIG. 6 is a perspective view of an alternate embodiment of FIG. 5.

Representing an alternate form of the soft-shell container for a unitized deodorizer, FIG. 6 discloses a sack-shaped deodorizer generally indicated by 36. Like the form shown in FIG. 5, the sack-shaped deodorizer 36 is comprised of one or more pieces of flexibly woven material 38 having a sealing tie 40 tightly wound around the gathered ends of the material 38. Like the form shown in FIG. 5, the material 38 may be either a natural blend or a synthetic, allowing air to enter but preventing compound (not shown) from escaping.

Figure 7:
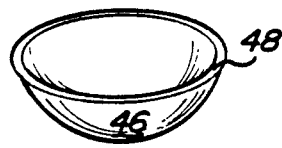
FIG. 7 is a perspective view of an alternate embodiment of a unitized deodorizer according to the present invention having a substantially resilient, semi-permeable container.
Figure 7A:
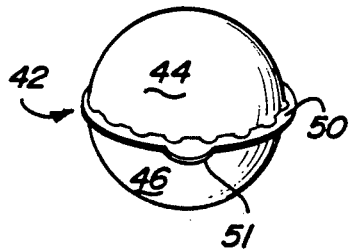
FIG. 7A is a perspective view showing one half of the container of FIG. 7 prior to assembly with another substantially identical half.

Referring to FIG. 7, another form of a unitized deodorizer is thereshown, generally indicated by 42. This form comprises two substantially identical halves including a first half 44 and a second half 46. The second half 46 is shown in FIG. 7A for clarity. Provided thereupon is an engaging lip 48 which is fitted about the periphery of the half 46, the half 44 (not shown) having a substantially identical lip 48' (not shown). Referring back to FIG. 7, the two halves are combined, with the compound (not visible) in between, one reversibly placed atop the other, so that the lip 48' (not visible) of the first half 44 abuts the lip 48 (not visible) of the second half 46. To fasten the halves 44, 46 to one another, a continuous sealing band 50 is wrapped around the peripheral lips 48, 48' (not visible). The band 50 may be replaced with or reinforced by other sealing methods, including stitching (not shown). To improve the utility of the deodorizer 42, a hook-eye 51 is provided on the band 50 thus allowing suspension by a hook, a string or the like.

To allow the entry of air into the halves 44, 46 but to prevent escape therefrom of the compound (not visible), a multitude of micro-apertures (not visible) are provided in each of the halves 44, 46 although the apertures may alternatively be provided in various sizes, such as illustrated in FIG. 3 as outer shell apertures 16 or as illustrated in FIG. 4 as container shell apertures 26, fitted with a mesh such as the mesh 28.

Figure 8:
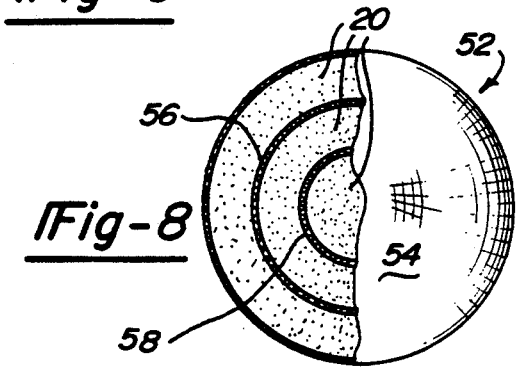
FIG. 8 is a perspective view of a further embodiment of the present invention having a substantially resilient container.

Referring to FIG. 8, yet another form of a unitized deodorizer is thereshown, generally indicated by 52. According to this form, there is provided a first shell 54 which encapsulates both the compound 20 and a plurality of concentrically provided inner shells which include a second shell 56 and a third shell 58. Of course, a greater or lesser number of inner shells may be used than is shown. Provided between the first shell 54 and the second shell 56 is the compound 20, as is provided between the second shell 56 and the third shell 58 as well as within the third shell 58. Each of the shells 54, 56, 58 is provided, like the halves 44, 46 of FIG. 7, with micro apertures (not visible) which allow for air to enter but which prohibit the escape of the compound 20.

Alternatively, the concentric shells may be substituted with multiple, orange-like sections or with a number of diamond-shaped inner units. Neither of these embodiments are shown.

Figure 9:
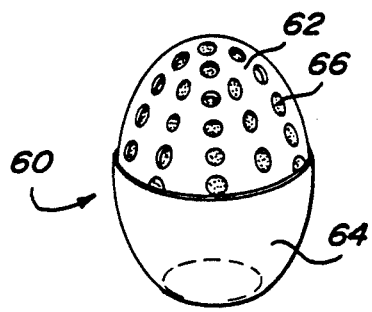
FIG. 9 is a perspective view of another embodiment of a unitized deodorizer of the present invention shown in partial cut-away view to reveal a plurality of concentric inner containers.

Referring lastly to FIG. 9, another form of a unitized deodorizer is shown, generally indicated by 60. For convenience, the deodorizer is generally egg-shaped allowing for placement in the egg holding portion of a refrigerator or the like. According to this form, the deodorizer 60 is comprised of an upper half 62 and a lower half 64. The upper half 62 is provided with a plurality of apertures 66, whereas the lower half 64 has no apertures. The deodorizer 60 has provided therein the compound (not visible) which is prevented from escaping by a mesh (not shown).

Having described the invention, however, many modifications thereto will become apparent to those skilled in the art to which it pertains without deviation from the spirit of the invention as defined by the scope of the appended claims.

I claim:

1. An article of manufacture for deodorizing one of selected places comprising:
   a preselected amount of a deodorizing compound having odor reducing characteristics;
   said deodorizing compound being provided in a substantially pulverized form and housed in a container;
   said container having a preselected shape; and
   said compound having surface area exposed to the atmosphere through said container;
   said container comprising a plurality of at least three concentric, ball-shaped shells of a substantially rigid material;
   said concentric shells being provided with a plurality of holes, said holes of one shell being non-aligned with holes of an adjacent shell;

said concentric shells being provided in spaced-apart relation to one another; and said deodorizing compound is provided in the spaces between said shells.

2. The article according to claim 1, wherein said deodorizing compound is substantially composed of sodium bicarbonate.

3. The article according to claim 1, wherein said deodorizing compound is a composition of deodorizing material and further includes a fragrance.

* * * * *